United States Patent [19]

Nicastro

[11] 4,393,519
[45] Jul. 19, 1983

[54] COMBINATION VISOR AND SWEATBAND

[76] Inventor: Norman J. Nicastro, 6210 E. Jenan, Scottsdale, Ariz. 85254

[21] Appl. No.: 243,793

[22] Filed: Mar. 16, 1981

[51] Int. Cl.³ .............................................. A61F 9/04
[52] U.S. Cl. ........................................... 2/12; 2/172; 2/DIG. 6; 2/DIG. 11
[58] Field of Search ..................... 2/12, 431, 426, 432, 2/451, 181, 185 B, 452, 195, 172, DIG. 11, DIG. 6

[56] References Cited

U.S. PATENT DOCUMENTS

| | | | |
|---|---|---|---|
| 137,032 | 3/1873 | Scharl | 2/172 |
| 1,434,854 | 11/1922 | Stall | 2/181 X |
| 2,342,377 | 2/1944 | Small | 2/12 |
| 2,385,405 | 9/1945 | Crowther | 2/12 |
| 2,406,598 | 8/1946 | Flood | 2/12 |
| 3,133,982 | 5/1964 | Janz | 2/426 X |
| 3,276,038 | 10/1966 | Fekete | 2/172 |
| 3,357,026 | 12/1967 | Wiegandt | 2/195 |
| 4,304,005 | 12/1981 | Danley, Sr. | 2/10 |
| 4,309,775 | 1/1982 | Jory | 2/432 X |

FOREIGN PATENT DOCUMENTS 482554 7/1953 Italy ......................................... 2/12

OTHER PUBLICATIONS

Gershman, "Self Adhering Nylon Tapes", 10-18-58, J.A.M.A., p. 930.

Primary Examiner—Peter Nerbun
Attorney, Agent, or Firm—Gregory J. Nelson

[57] ABSTRACT

A combination visor and sweatband for protecting the eyes and surrounding peri-ocular areas and for absorbing and evaporating perspiration from the upper facial area is disclosed. The combination visor and head band includes an absorbent, elastic sweatband encircling the head of the user. A visor is secured to the lower edge of the sweatband extending downwardly adapted to shade the eyes of the user. The head band is cooperable with detachable fasteners on the eyeshield so the visor may be secured to the eyeshield. In one embodiment, bendable stays are imbedded in the material of the visor so that the visor can be conformed to any shape desired by the user. In another embodiment, the depending visor extends annularly around the entire lower edge of the sweatband so the sweatband can be rotated when the portion at the user's forehead becomes saturated with moisture.

8 Claims, 13 Drawing Figures

COMBINATION VISOR AND SWEATBAND

The present invention relates to a combination visor and sweatband and more particularly relates to special headgear for absorption of perspiration from the brow of the user and for providing peri-ocular protection against solar radiation.

It is a common practice for individuals engaged in strenuous activity such as jogging, basketball, tennis and other racket sports to wear absorbent head bands. These head bands usually consist of an elasticized cotton material which is adapted to encircle the head of the user to absorb perspiration primarily on the brow of the user and to prevent droplets of perspiration from coming into contact with the eyes of the user. Various modifications to the basic head band construction can be found in the prior art. For example, U.S. Pat. No. 1,434,854 shows a sweatband including a pouch with absorbent material which is removable from the pouch. The absorbent pad may be washed or substituted by a clean pad when necessary.

One particular shortcoming of head bands of the general type described above is that these head bands while serving to absorb moisture and perspiration do not offer any substantial protection to the user from solar radiation and are not compatible with eyeglasses. The few prior art designs which incorporate some type of eye protection with a head band generally have not received wide acceptance as being complicated and not practical in use. For example, U.S. Pat. No. 3,133,982 shows a sweat band specially designed for use with eyeglasses including a block of compressible sponge material which is insertable between the eyeglass frame and the brow of the wearer.

Accordingly, it appears that there clearly exists a need for a combination visor and sweatband which will serve to absorb and deflect perspiration and at the same time provide protection against harmful solar radiation. The total amount of exposure to solar radiation required to produce irreversible damage to the peri-ocular and ocular structures is not precisely known. It is known that with each subsequent exposure to the sun, irreversible damage to the structures can occur. Accordingly, it is a primary purpose of the present invention to provide a combination visor/sweatband which will minimize the effects of ultraviolet and infrared radiation on the eye and its surrounding areas by providing a combination visor and sweatband element which will specifically cooperate with an eye shield and assist in stabilizing the eyeshield.

Briefly, the combination visor and sweatband of the present invention includes a specially constructed head band having an upper sweatband segment which encircles the head. The sweatband portion is constructed of a suitable material such as elasticized wool or cotton can be stretched about the head of the user. The visor component is secured to the head band to be worn over the eyes of the user. The visor is provided with securement means for releasably attaching the lower edge of the visor to a portion of the frame of the wearer's eyeglasses. In other embodiments of the present invention, the sweatband can be provided with a sleeve to receive a removable insert. The visor may be flexible and provided with bendable stays in the material so that the visor can be formed into any desirable shape. The visor material is sun-blocking and the material of both the head band and visor is absorbent and is selected to aid in evaporation.

The above and other objects and advantages of the present invention will become more apparent from the following description, claims and drawings in which:

As pointed out above, exposure to solar radiation produces irreversible damage to the peri-ocular skin and therefore, individuals engaged in outdoor activities should take care to minimize the effects of ultraviolet and infrared radiation on the eye and the surrounding areas. Further, individuals engaged in strenuous activities often perspire vigorously. The formation of perspiration particularly on the forehead as this accumulation of perspiration will tend to flow toward the eye areas of the user causing irritation to the user.

Figure 1:
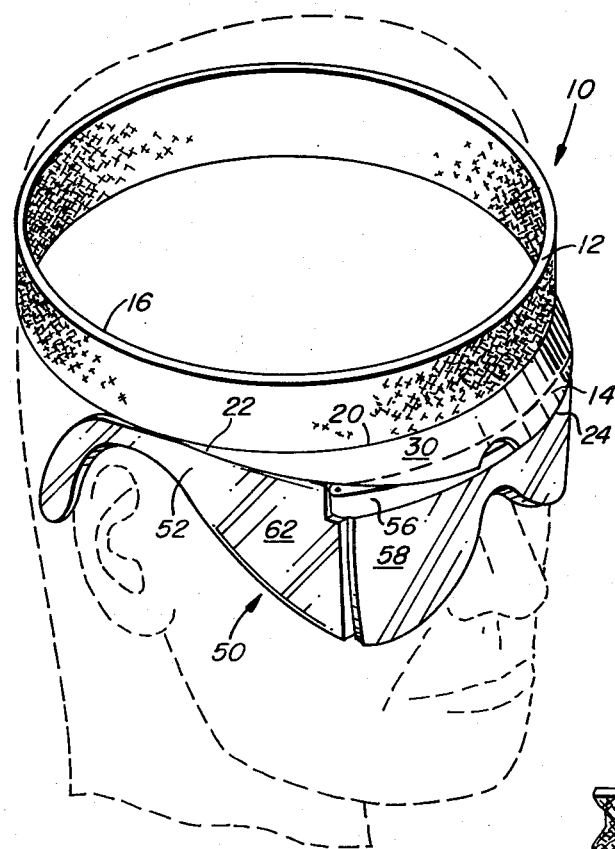
FIG. 1 is a perspective view showing a preferred form of the visor/head band of the present invention applied to eyeglasses of the user.
Figure 2:
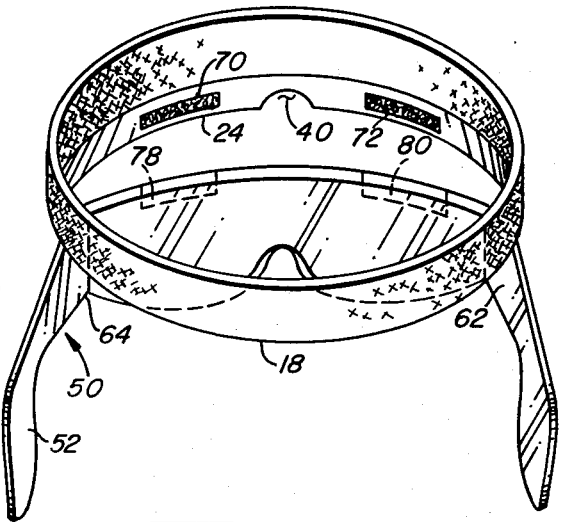
FIG. 2 is a rear perspective view of the visor/head band in association with a pair of eyeglasses.

Turning now to the drawings, particularly FIGS. 1 and 2, the combination visor and head band of the present invention is shown and is generally indicated by the numeral 10. For convenience of reference throughout this specification, the combination visor/head band of the invention will be designated simply "head band." Head band 10 includes a head encircling sweatband portion 12 and a visor portion 14. The sweatband portion 12 is in the form of an annular band constructed of a highly absorbent fabric such as wool or cotton, preferably having an elastic characteristic so that it can be expanded to snugly encircle the head of the user. The material should have the characteristics of being suitably light-weight and also provide suitable evaporative qualities for rapid drying. Preferably, the sweatband portion is approximately 1½ to 2 inches in width depending upon the preference of the user. This allows the upper portion of the head or cranium of the user to remain exposed which is desirable particularly in strenuous activity since approximately 65% of the body heat is transferred from this area of the head. Sweatband 12 is provided with an upper edge 16 and a lower edge 18 and is generally worn as shown in FIG. 1.

Visor 14 is secured to the lower edge 18 of the sweatband at seam 20. Visor 14 extends along the lower edge 18 of the sweatband in an area corresponding to the forehead of the user and preferably extends a sufficient distance to extend to an area anterior to the ear of the user when worn terminating at 22. The lower edge 24 of the visor extends from terminus 22 tapering downwardly having an intermediate portion 30 adapted to extend across the forehead of the user. The opposite lateral side of the visor tapers upwardly joining the head band at 22.

The medial area of the visor is designated by the numeral 30. The lower or inferior edge 24 of the visor in the medial area may be provided with an arcuate recess 40 for ventilation and admission of air.

The head band 10 of the present invention is adapted to be used with eyeglasses as indicated in FIG. 1. The term "eyeglasses" and "eyeshield" are used interchangeably throughout. The eyeglasses are generally designated by the numeral 50 and include opposite temple frames 52 which support front frame 56. A pair of lenses 58 are supported in the frame 56 and may be tinted to provide protection against damaging solar radiation. Further eyeglasses 50 are provided with shields 62 and 64 opposite lateral sides of the glasses attached to the anterior portion of the temple frames 52. Glasses of this type are sold under the trademark NOIR or those sold by Orcolite under the designation UV400. These type glasses may be worn over optically corrective glasses.

In order to more fully shield the peri-ocular area of the user, the lower or inferior edge 24 of the medial portion 30 of the visor is detachably securable to the frame of eyeglasses 50. To provide securement, the inner face of the medial portion of the visor may be provided with several strips 70 and 72 of material comprising one portion of loop and pile fastener of the type, for example, as sold under the trademark Velcro. Fastener strip 70 and 72 are arranged adjacent the inferior edge of the visor and located on opposite sides of ventilation recess 40.

Cooperating fastener members 78 and 80 respectively are secured to the outer surface of eyeglass frame 56 above the lenses 58. Preferably, the cooperating fastener members 78 and 80 are positioned in a slight recess in the frame 56 adapted to accomodate the fastener members.

FIG. 1 best shows the position of the head band 10 and the eyeglasses in place. The head band 10 of the present invention is then pulled over the head of the user expanding to snugly encircle the head. The visor 14 is positioned at the front so that fastener members 70 and 72 are vertically aligned with cooperating fastening members 78 and 80 on the front eyeglass frame 56. Once aligned, the cooperative fastener members can be engaged by application of slight pressure. The visor 14 then fully extends from the head to the eyeglass frame in the frontal area and extends laterally at the temple frames to provide a barrier against solar radiation for the protection of the eyes & their surrounding structure laterally. The sweatband 12 serves to absorb perspiration and moisture generated by the user. The band can easily be removed by separating the removable fasteners and pulling the band from the user's head. The visor itself can be constructed from any of a number of materials, preferably the material having light-blocking characteristics and having suitable elastic and absorbent qualities to compliment the sweatband. Further, the material of the visor should be easily launderable so that the entire head band can be washed when required.

Figure 3:
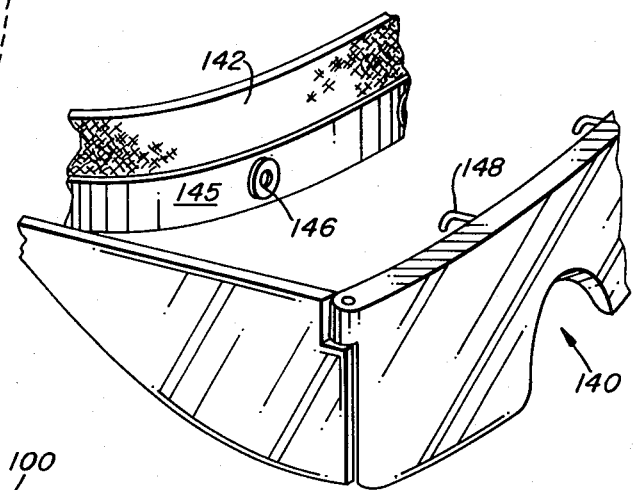
FIG. 3 is an enlarged detail view illustrating an alternate means of detachably securing the visor/head band to the wearer's eyeglasses.
Figure 4:
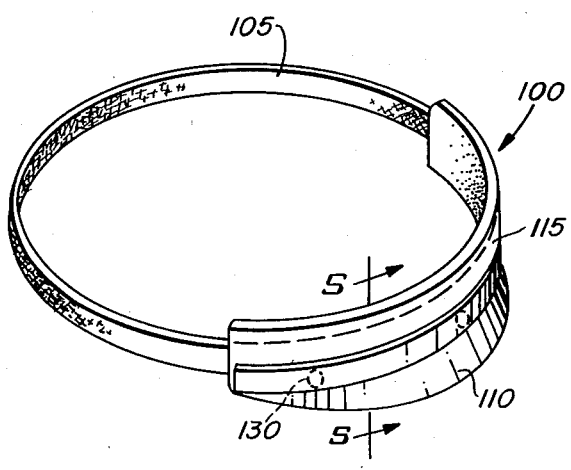
FIG. 4 shows a further modification of the present invention.
Figure 5:
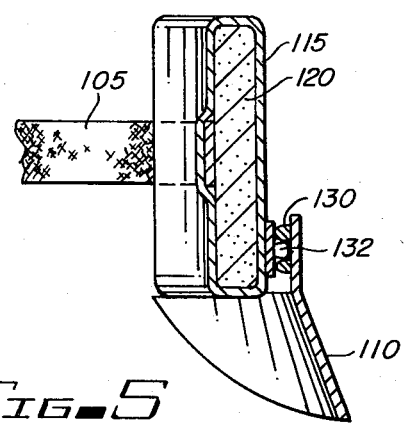
FIG. 5 is a sectional view taken along line 5—5 of FIG. 4.
Figure 6A:
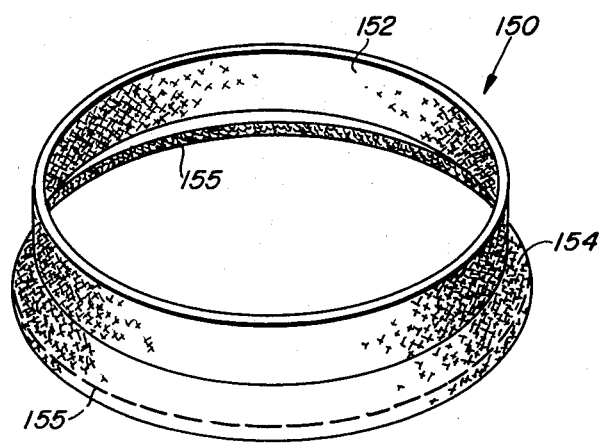
FIG. 6A is a perspective view of still another embodiment of the present invention.

Turning now to FIGS. 4 and 5, an alternative embodiment of the present invention is illustrated. This embodiment, generally designated by the numeral 100 is generally constructed as discussed with respect to FIGS. 1 to 3 having an elastic head encircling band 105 and a depending visor 110 secured to the head band in the frontal area. The head band 105 is provided with an annular sleeve 115 extending at least along the frontal area above the visor. Sleeve 115 is adapted to receive an absorbent insertable pad 120. When the pad 120 becomes saturated, it may be removed and replaced with a clean and dry pad for better moisture absorption. In this embodiment, the visor 110 is detachably secured to the band 105. The upper edge of visor 110 carries several female snap fasteners 130 which are engageable with male snap fastener member 132 extending from the lower edge of pouch or sleeve 115 in the frontal area. Therefore, the sweatband can, if desired, be used without the visor or a single visor can be cooperatively used with bands of various sizes and/or colors according to the preference of the user.

FIG. 3 illustrates an alternate construction for attaching eyeglasses 140 to head band 142. Head band 142 is as has been generally described with reference to FIGS. 1 and 2 as is an elasticized, absorbent head encircling member. Visor 145 depends from the band 142 at least in the frontal area. Projections 148 extend from the frame of eyeglasses 142 and are engageable in cooperating eyelets 146 in the visor 145. The user can also engage the visor 145 and eyeglasses or eyeshield 140 by inserting projections 148 in the intersticial areas of the woven fabric of visor 145.

FIGS. 6A, 6B, 7A and 7B show still another embodiment of the present invention which is generally designated by the numeral 150. In embodiment 150, head band 152 is adapted to continuously expand to encircle the head of the user and fit as has been described. Visor portion 154 is secured to the lower edge of the head band 152 and extends annularly about the lower edge of the band. Visor 152 is shown as being provided on the interior with a continuous annular band 155 of one of a cooperative loop and pile member which is adapted to cooperate with mating members on the eyeshield frame as has been described with reference to FIGS. 1 and 2. Alternatively, of course, the visor could be adapted to be engaged on cooperative projections or grips on the eyeglass frame as has been described with reference to FIG. 3.

Figure 7A:
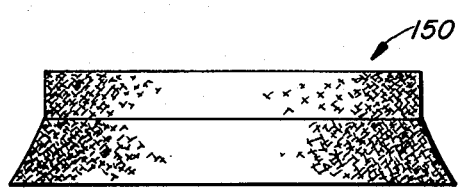
FIGS. 7A and 7B are side views corresponding to FIGS. 6A and 6B, respectively.
Figure 7B:
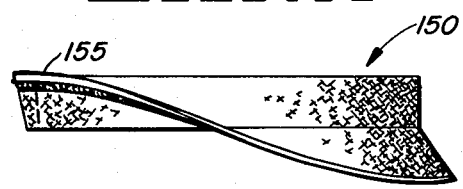
Figure 6B:
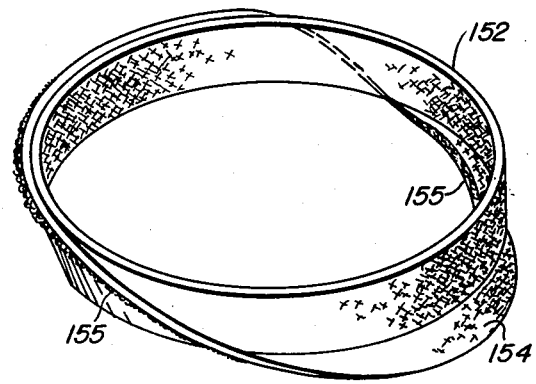
FIG. 6B is a perspective view similar to FIG. 6A with a portion of the visor in a folded position.

With the head band of this embodiment, the head band can be worn in a position with one portion of the visor 154 in the frontal position shading the eyes of the user. When the sweatband portion becomes saturated with moisture, the head band can be rotated, bringing another portion of the visor into position over the user's eyes. For example, the portion of the head band 152 formerly in the occipital area of the user will be substantially dry and will be capable of absorbing additional moisture. The visor portion now positioned at the rear of the head of the user, may be folded upwardly as shown in FIGS. 6B and 7B occupying an out-of-the-way position against the head band if desired by the user. The fastener band 155 is continuous and may be secured to a cooperating member at any location around the band. If the visor material has sufficient elasticity, the visor may be simply stretched over the frames of eyeglasses to secure them in place to prevent dislodgement during physical activity.

Figure 8:
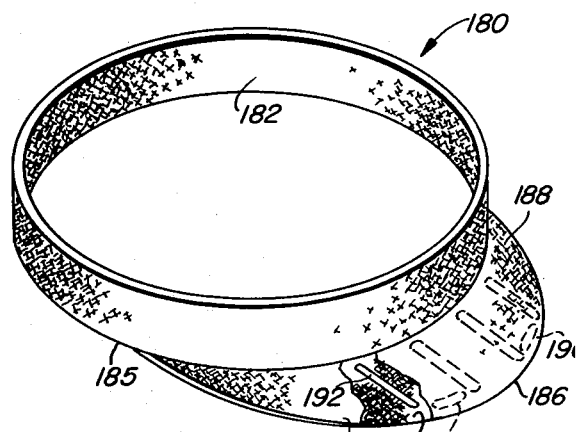
FIG. 8 shows still another modification of the present invention.

FIG. 8 is illustrative of still another embodiment of the present invention which is generally designated by the numeral 180. The combination visor and head band 180 has a band portion 182 which is elastic adapted to expandably encircle the head of the user as has been described having the ability to absorb moisture. Visor 184 is secured to the lower edge 185 of the sweatband by stitching or adhesive. The visor has a generally arcuate outer edge 186 which tapers at opposite lateral sides joining the lower edge of the sweatband. The material of the visor is suitable, flexible woven material having a top and bottom layer 188 and 190 or is a flexible synthetic such as a low-density, resinous foam. Interposed between the inner and outer layers 188 and 190 are a plurality of bendable stiffeners or stays 192. The stiffeners or stays may be of a flexible material such as aluminum or plastic which can be deformed to various shapes. Thus, by deforming the stays imbedded within the layers of material in the visor, the visor can be shaped to the particular requirements of the user consistent with the sun conditions, user's preference and anatomical shape of the user's face. The visor of this embodiment is particularly applicable to provide shade with or without the accompanying eyeglasses. Loop and pile fasteners 196 and 198 are provided on the inner side of the visor for attachment to a cooperable eyeshield as has been described. Thus, a wide range of adjustability is obtainable by the user simply shaping the visor as required.

Figure 9:
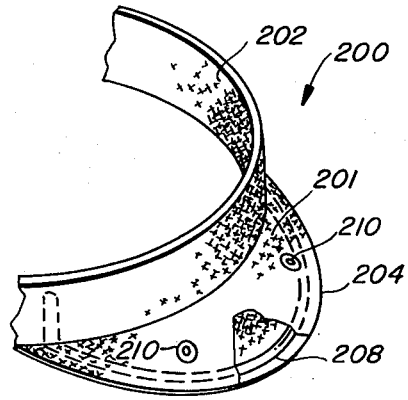
FIG. 9 is a partial view illustrating another modification of the visor of the present invention.

In FIG. 9, illustrative of another modified form of the head band/visor, is designated by the numeral 200. Flexible visor 201 is secured to band 202. Visor 201 has an arcuate leading edge 204. A bendable wire stay 208 extends within the material of the visor adjacent edge 204 so the visor can be appropriately shaped. Eyelets 210 accomodate attachment to an eyeshield of the type shown in FIG. 3.

Figure 10:
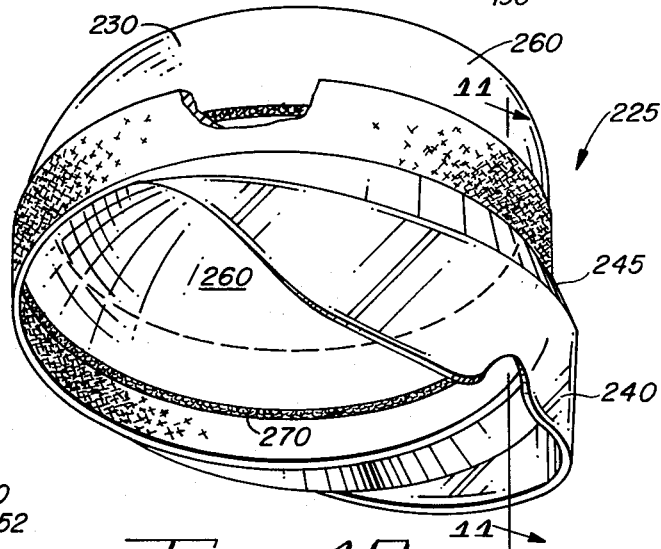
FIG. 10 is a bottom perspective view of the visor/head band with integrally formed eyeglasses.
Figure 11:
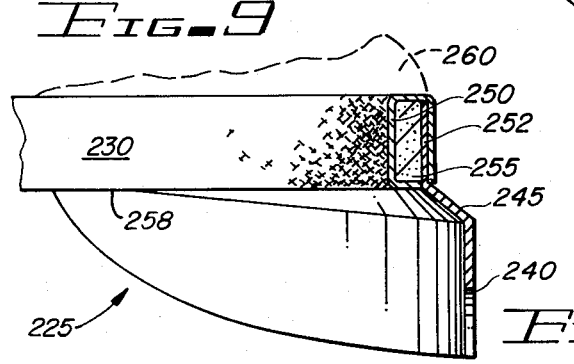
FIG. 11 is a sectional view taken along lines 11—11 of FIG. 10.

In FIGS. 10 and 11, embodiment 225 includes an elastic, absorbent band 230 shown as being multiple layers 250 and 252 and containing a filler 255 for greater absorbent capacity. Flexible visor section 245 extends from the lower edge 258 of band 230. Eyeshield member 240 is permanently or removably attached to lower edge 246 of visor 245. Eyeshield 240 is configured having a transparent lens projecting in front of the eyes of the wearer and extending laterally to fully shield the peri-ocular areas. Eyeshield 240 may be appropriately tinted to reduce the effect of infrared and ultraviolet radiation. The flexible visor serves to shield solar radiation from entering the area above the eyeshield and further permits the user to position the eyeshield as desired. For use in cold weather, cranial cap 260 may be secured at loop and pile fastener 270 at the interior of the band to minimize heat loss from the head of the user.

It will be obvious to those skilled in the art to make various modifications, alterations and changes to the various embodiments of the invention described herein. For example, the material of construction of the head band including the sweatband and visor portions can be selected from a wide variety of existing fabrics and materials. Similarly, various types of cooperable fasteners can be used to secure the visor portion to cooperating eyeglasses. The particular location of the cooperating fasteners on the visor and the cooperating glasses can be varied consistent with the needs and dictates of the user. Also, various styles and types of eyeglasses can be used in conjunction with the visor. The glasses may have corrective lenses and may be tinted or clear for outside or inside use. The location of the cooperative fastener of the glasses can also be variously positioned in accordance with the dictates and preference of the user. For example, in some instances, it may be desirable to place the cooperative fastener on the flat upper edge of the lens frames in contrast to the location shown in FIG. 1.

The head band of the present invention serves a primary purpose of protecting the eyes and surrounding peri-ocular areas from harmful effects of solar radiation. Particularly when used in conjunction with tinted eyeglasses or eyeshields. The sweatband also provides a means of absorbing evaporation and perspiration from the upper facial area while also providing a brace for the securement of the eyeshield to the face.

The head band of the present invention leaves the major portion of the head uncovered for promoting heat loss from the body. The eyeglasses may be tinted or for maximum protection against ultraviolet and infrared radiation or may be provided with clear lenses for indoor activities and jobs in which protective eyeshields are recommended. In some instances, the width and configuration of the sweatband portion may further include a cap to cap the cranial area for use in cold locations where containment of heat is an important consideration.

It will be obvious to those skilled in the art to make various changes, modifications and alterations to the combination visor and sweatband of the present invention. To the extent that these various changes, alterations and modifications do not depart from the spirit and scope of the appended claims, they are intended to be encompassed therein.

I claim:

1. Headgear adapted for use with an eyeshield of the type including eye protecting lenses supported on a lens frame worn by a user, said headgear comprising:
   (a) a head band adapted to encircle the head of the user and positionable in retained relationship thereon on a person's head, at least a portion of said head band being constructed of a material which is elasticized and stretchable and moisture absorbent said portion forming a section adapted to bear on and closely conform to the forehead of the user;
   (b) a flexible visor attached to said head band at said section and extending along its entire length from the head band forwardly therefrom, said visor having an outer edge;
   (c) fastener means on said visor adapted to engage the said lens frame whereby said visor is extendable and securable between the head band and said frame to form a protective shield fully extending in the peri-ocular area between the forehead of the user and the frame, with said eye protecting lenses held in a position whereby moisture accumulation on the lenses is minimized and the entire peri-ocular area is substantially shielded from solar rays.

2. The headgear of claim 1 wherein said fastener means comprises one of a loop and pile fastener on said visor and the other of a loop and pile fastener on said frame whereby said visor is detachably securable to said eyeshield.

3. The headgear of claim 1 wherein said head band includes a receptacle therein in said section adapted to removably receive an absorbent pad.

4. The headgear of claim 1 wherein said eyeshield includes projection means thereon adapted to engage said fastener means on said visor.

5. The headgear of claim 1 wherein said visor extends circumferentially about said head band and whereby a portion thereof at the rear of the user's head when worn is adapted to be reversibly folded to a position in juxtaposition with said head band.

6. The headgear of claim 1 wherein said visor includes shapable stays therein whereby said visor can be shaped as desired by the user.

7. An eyeshield for protecting the peri-ocular area of the user comprising:
   (a) a head band adapted to encircle the head of the user and positionable in a retained relationship about a person's head, at least a portion of said head band being constructed of a material which is absorbent and has elastic qualities, said moisture-absorbing portion forming a section adapted to bear on and closely conform to the forehead of the user;
   (b) an eyeshield attached to said head band and extending therefrom, said eyeshield having a visor portion extending along its entire length from the lower edge of said head band to shield the peri-ocular area of the user, said visor having a lower edge, said visor portion having an upper edge and a lower edge, said lower edge extending below said upper edge in normal use of the eyeshield;
   (c) said eyeshield having a portion extending substantially vertically downward from the lower edge of said visor portion and extending laterally to provide a barrier against solar radiation for the protection of the eyes and their surrounding structure, said shield having ultraviolet blocking characteristics.

8. The eyeshield of claim 7 wherein said visor extends forwardly and downwardly from said headband.

* * * * *